United States Patent [19]
Sullivan et al.

[11] Patent Number: 5,424,458
[45] Date of Patent: Jun. 13, 1995

[54] INTEGRATED PRODUCTION OF PROPYLENE OXIDE AND METHYL T-BUTYL ETHER

[75] Inventors: Gordon A. Sullivan, Princeton Jct., N.J.; Herry E. Eilerts-de Haan, Gerrards Cross, England; William J. Piel, Media; John J. Leonard, Springfield, both of Pa.

[73] Assignee: Arco Chemical Technology, L.P., Grennville, Del.

[21] Appl. No.: 207,578

[22] Filed: Mar. 8, 1994

[51] Int. Cl.6 .................. C07D 301/19; C07D 303/04; C07C 41/06
[52] U.S. Cl. ................................. 549/529; 568/697; 568/698
[58] Field of Search .......................... 549/529; 585/654

[56] References Cited
U.S. PATENT DOCUMENTS

| | | | |
|---|---|---|---|
| 3,383,431 | 5/1968 | Fishel | 585/654 |
| 4,988,830 | 1/1991 | Gelb et al. | 549/529 |
| 5,008,414 | 4/1991 | Ramachandran et al. | 549/532 |
| 5,157,161 | 10/1992 | Knifton | 568/698 |
| 5,160,424 | 11/1992 | Le et al. | 585/654 |
| 5,220,092 | 6/1993 | Clark et al. | 585/654 |

*Primary Examiner*—Joseph E. Evans
*Attorney, Agent, or Firm*—William C. Long

[57] ABSTRACT

The present invention provides a novel integration of an existing MTBE process unit with new propylene oxide producing facilities whereby through this integration new propylene oxide production is achieved without significant increase in MTBE production.

2 Claims, 1 Drawing Sheet

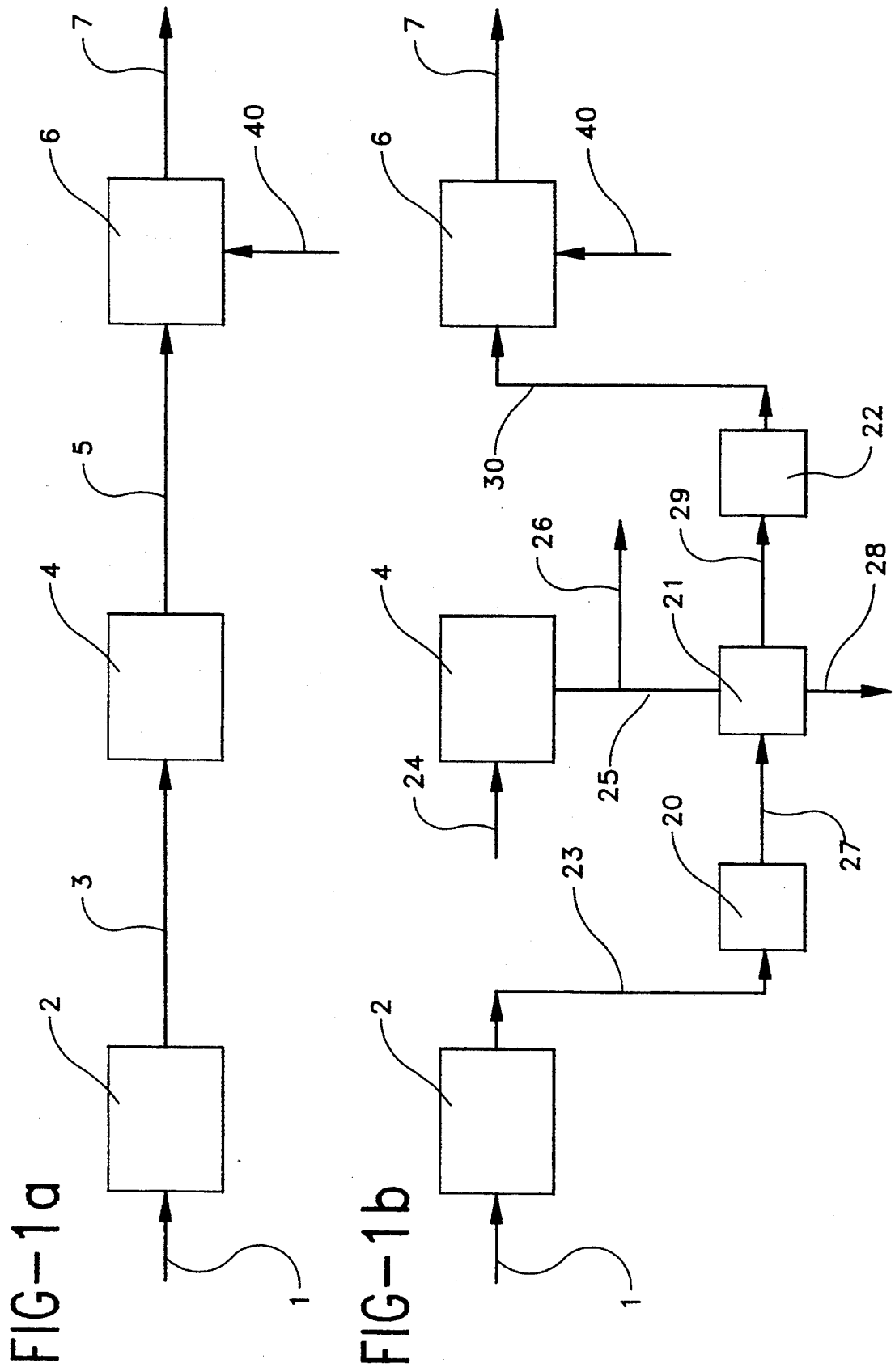

INTEGRATED PRODUCTION OF PROPYLENE OXIDE AND METHYL T-BUTYL ETHER

BACKGROUND OF THE INVENTION

1. Field of the Invention

The present invention provides for the novel integration of a propylene oxide production sequence with an existing methyl tertiary butyl ether (MTBE) process unit whereby propylene oxide can be economically produced without the need for MTBE production beyond that already produced in the existing unit.

2. Description of the Prior Art

An important commercial process for the production of propylene oxide involves the reaction of propylene with tertiary butyl hydroperoxide (TBHP) with the formation of propylene oxide and tertiary butyl alcohol (TBA). The co-product tertiary butyl alcohol is frequently dehydrated to isobutylene which is converted to methyl tertiary butyl ether, a product which has utility as a gasoline additive.

Another method which is in commercial practice for the production of methyl tertiary butyl ether involves the dehydrogenation of isobutane to isobutylene, and the etherification of the isobutylene with methanol to MTBE.

A problem exists with the relative supply and demand of propylene oxide and MTBE. At the present time there is an overcapacity for MTBE based on the demand for this material while additional propylene oxide capacity is needed. This imbalance in the supply and demand for these chemicals has created serious problems for those seeking to expand propylene oxide production while avoiding unwanted expansion of MTBE production.

BRIEF DESCRIPTION OF THE INVENTION

The present invention represents a solution to the above problems by providing a novel integration of an existing MTBE process unit with new propylene oxide producing facilities whereby through this integration the desired new propylene oxide production is achieved without significant increase in MTBE production. Specifically, the isobutane which normally would be dehydrogenated in the conventional MTBE process is instead diverted to an oxidation unit where it is converted to tertiary butyl hydroperoxide in accordance with known procedures. A source of propane, which is a relatively inexpensive material, is fed to the existing isobutane dehydrogenation unit and converted therein to propylene. At least a portion of this propylene is reacted with the tertiary butyl hydroperoxide from the oxidation unit to form product propylene oxide in accordance with known technology as well as co-product tertiary butyl alcohol. The co-product TBA can be dehydrated to isobutylene which is then converted in the existing etherification unit to MTBE, or alternatively the TBA can be reacted directly in the etherification unit with methanol to form MTBE.

In this way the desired new propylene oxide production can be achieved with minimum capital requirements and without the addition of new MTBE capacity to a market which already has more than enough MTBE capacity available using inexpensive propane as the $C_3$ hydrocarbon source.

DESCRIPTION OF THE DRAWING

FIG. 1a shows in diagrammatic form a conventional MTBE process.

FIG. 1b shows the novel integrated process of the invention in diagrammatic form.

DETAILED DESCRIPTION

A conventional MTBE production facility is illustrated in FIG. 1a. Illustratively, a butane stream in amount of about 380 thousand metric tons per year is fed via line 1 to isomerization and separation zone 2. In zone 2, by conventional procedures, n-butane is isomerized to isobutane and the net isobutane is separated and passed via line 3 to dehydrogenation zone 4. Net isobutane passing to zone 4 is about 370 thousand metric tons per year.

In zone 4, the isobutane is dehydrogenated in accordance with known procedures to form about 330 thousand metric tons per year of isobutylene which is separated and transferred via line 5 to etherification zone 6 wherein the isobutylene is reacted with about 185 thousand metric tons per year of methanol introduced via line 40 at etherification conditions. Product MTBE in amount of about 500 thousand metric tons per year is recovered via line 7.

In practice of the present invention, the MTBE facility of FIG. 1a is modified as indicated in FIG. 1b. Specifically, oxidation zone 20, epoxidation zone 21 and dehydration zone 22 are integrated in the manner shown with existing zones 2, 4 and 6. Referring to FIG. 1b, the 370 thousand metric tons per year of isobutane produced as above indicated passes from zone 2 via line 23 to oxidation zone 20 wherein it is converted by liquid phase non-catalytic reaction with molecular oxygen to a tertiary butyl alcohol (TBA) and tertiary butyl hydroperoxide (TBHP) mixture comprised of about 270 thousand metric tons per year TBHP.

Propane in amount of about 300 thousand metric tons per year passes via line 24 to dehydrogenation zone 4 wherein in accordance with known procedures the propane is dehydrogenated to propylene. The net of about 250 thousand metric tons per year of propylene is removed via line 25 from zone 4, and an excess of about 110 thousand metric tons over the amount needed for epoxidation is recovered via line 26 as an important and valuable product of the integrated process. The remaining 140 thousand metric tons per year passes to epoxidation zone 21 wherein by known procedures the propylene is reacted with the 270 thousand metric tons per year of TBHP, which passes to zone 21 via line 27, to form propylene oxide. Product propylene oxide together with some formed propylene glycol is recovered in amount of about 175 thousand metric tons per year via line 28.

Tertiary butyl alcohol formed both in oxidation zone 20 and in epoxidation zone 21 passes in amount of about 440 thousand metric tons per year via line 29 to dehydration zone 22 wherein the TBA is dehydrated to isobutylene in accordance with well known procedures. The formed isobutylene in amount of about 330 thousand metric tons per year passes via line 30 to etherification zone 6 wherein it is converted to MTBE by reaction with 185 thousand metric tons per year of methanol introduced via line 40 as above described. Product MTBE is likewise recovered via line 7 in amount of about 500 thousand metric tons per year.

From the above illustrative analysis, it can be seen that the integration according to the invention enables the original MTBE production rate to be maintained while providing for the new production of 175 thousand metric tons per year of propylene oxide and 110 thousand metric tons per year of propylene. Costs associated with the process integration involve essentially only the provision of the isobutane oxidation zone, the epoxidation zone, and the dehydration zone together with the appropriate separation and recovery apparatus.

The isobutane oxidation step which converts isobutane to tertiary butyl hydroperoxide is carried out in accordance with known procedures. Methods are known for the production of TBHP by the non-catalytic molecular oxygen oxidation of isobutane at elevated temperature and pressure. in this regard, attention is drawn to U.S. Pat. No. 2,845,461 of Winkler, et al., to U.S. Pat. No. 3,478,108 of Grane and to U.S. Pat. No. 4,408,081 of Foster, et al. Isobutane is reacted with oxygen to produce TBHP along with TBA. The isobutane oxidation reaction conditions in oxidation reactor are those which are normally used for this reaction as described, for example, in Winkler, et al. U.S. Pat. No. 2,845,461. Generally, reaction temperatures in the range of 100° C. to 200° C. preferably 120° C. to 150° C. are employed. Pressures in the range of 200 to 500 psig, preferably 300 to 450 psig are employed. Residence times in the oxidation zone of 3 to 15 hours, preferably 5 to 10 hours are suitable. It is preferred to use oxygen as the oxidant, although the use of oxygen in admixture with minor amounts of an inert gas such as nitrogen can be used.

The dehydrogenation of isobutane to isobutene and propane to propylene are very analogous reactions. With only minor modifications the isobutane dehydrogenation unit from the existing MTBE process can be converted to use for the dehydrogenation of propane to propylene.

Generally speaking the dehydrogenation is carried out in accordance with known procedures. Catalysts such as chromium on alumina, platinum on alumina and the like are used. Dehydrogenation conditions include temperatures of 600° to 700° C., pressures of 1 to 40 psig. An illustrative description can be found in U.S. Pat. No. 5,146,034.

The isobutane dehydrogenation unit employed in practice of the invention is generally capable of producing propylene in excess of the amount needed to react with the tertiary butyl hydroperoxide. Generally speaking, the MTBE production in the existing unit will dictate how much isobutane is charged to the oxidation unit and this, in turn, will dictate the amount of propylene needed to react with the formed tertiary butyl hydroperoxide. Generally, a substantial excess of propylene is formed in the dehydrogenation unit over that needed, and the excess propylene forms a valuable product of the process as described above.

In the epoxidation unit, propylene and tertiary butyl hydroperoxide are reacted in accordance with known procedures to form propylene oxide and tertiary butyl alcohol. Suitable reaction conditions are described, for example, in U.S. Pat. No. 3,351,635.

The dehydration of TBA to isobutylene is carried out in accordance with known procedures. Suitably, a catalyst such as alumina is employed and the reaction is carried out in the vapor phase. See U.S. Pat. No. 4,036,905 which describes isobutane oxidation to TBHP, propylene epoxidation with the TBHP, and separation and dehydration of TBA to isobutylene.

Likewise, the conversion of isobutylene to MTBE is carried out in accordance with known procedures and the existing etherification unit and conditions are employed. See for example, U.S. Pat. No. 5,276,212.

In place of the separate TBA dehydration and isobutylene etherification, the direct conversion of TBA to MTBE by known procedures can be carried out. The one step conversion of TBA and methanol to MTBE is described, for example, in U.S. Pat. Nos. 4,827,048, 5,081,318, 5,157,161, 5,179,052, 5,183,947, 5,214,217, 5,215,218, 4,918,244, 4,925,989, and 5,220,078.

As above indicated, each of the separate reaction steps is known and is carried out in accordance with conventional procedures. The essence of the invention resides in the novel integration of these steps which results in the process of the invention.

The following example illustrates the invention:

In this example, an existing 500 million pound per year MTBE unit is integrated with new isobutane oxidation, propylene epoxidation and TBA dehydration facilities in accordance with the invention.

Isobutane is fed to the oxidation zone at the rate of 370 thousand metric tons per year and therein oxidized with molecular oxygen in the liquid phase at 150° C. and 450 psig to form 270 thousand metric tons per year TBHP and 200 thousand metric tons per year TBA.

Propane is fed to the dehydrogenation unit at the rate of about 300 thousand metric tons per year and therein is dehydrogenated in the vapor phase by contact with chromium on alumina catalyst at 700° C. and 20 psig. About 250 thousand metric tons per year of propylene product are recovered. Hydrogen in amount of about 12 thousand metric tons per year is also recovered.

The TBHP and TBA mixture from the oxidation zone is recovered and fed to the epoxidation zone at the rate of about 470 thousand metric tons per year. About 140 metric tons per year of propylene are also fed to the epoxidation zone, the remaining 110 thousand metric tons per year of propylene comprising a product of the process.

In the epoxidation zone, propylene and TBHP are reacted in the liquid phase at 120° C. and 500 psig in the presence of a soluble molybdenum catalyst (25 ppm) to form propylene oxide.

The reaction mixture is distilled in accordance with known procedures and about 175 thousand metric tons per year of propylene oxide is recovered. TBA in amount of about 440 thousand metric tons per year is passed to the dehydration zone and therein dehydrated in the vapor phase over a porous high surface are alumina at 390° C. and 200 psig. Resulting isobutylene in amount of about 330 thousand metric tons per year is passed to the etherification one and therein reacted with about 185 thousand metric tons per year of methanol to form 500 million pounds per year MTBE product. The etherification is carried out at 50° C. and 200 psig, and a sulfonic acid resin catalyst is employed.

We claim:

1. The method for the modification of a process sequence of dehydrogenation of isobutane to isobutylene in a dehydrogenation zone and reaction of the isobutylene with methanol in an etherification zone to form methyl tertiary butyl ether, which method comprises diverting the said isobutane from the dehydrogenation zone to an oxidation zone and therein oxidizing the diverted isobutane to tertiary butyl hydroperoxide, feeding propane to said dehydrogenation zone and therein dehydrogenating the propane to propylene, reacting said tertiary butyl hydroperoxide and said propylene in an epoxidation zone to form propylene oxide and tertiary butyl alcohol, recovering said propylene oxide, dehydrating said tertiary butyl alcohol to isobutylene in a dehydration zone, and reacting the isobutylene, formed by the dehydration of the tertiary butyl alcohol, with methanol in said etherification zone to form methyl tertiary butyl ether.

2. The method for the modification of a process sequence of dehydrogenation of isobutane to isobutylene in a dehydrogenation zone and reaction of the isobutylene with methanol in an etherification zone to form methyl tertiary butyl ether, which method comprises diverting the said isobutane from the dehydrogenation zone to an oxidation zone and therein oxidizing the diverted isobutane to tertiary butyl hydroperoxide, feeding propane to said dehydrogenation zone and therein dehydrogenating the propane to propylene, reacting said tertiary butyl hydroperoxide and said propylene in an epoxidation zone to form propylene oxide and tertiary butyl alcohol, recovering said propylene oxide, and reacting the said tertiary butyl alcohol with methanol in said etherification zone to form methyl tertiary butyl ether.

* * * * *